United States Patent [19]

Komatsu et al.

[11] 4,346,232

[45] Aug. 24, 1982

[54] PROCESS FOR PRODUCING AROMATIC POLYCARBOXYLIC ACID

[75] Inventors: Makoto Komatsu; Toru Tanaka; Hideaki Fujita, all of Kurashiki, Japan

[73] Assignee: Mitsubishi Gas Chemical Company, Inc., Tokyo, Japan

[21] Appl. No.: 177,183

[22] Filed: Aug. 11, 1980

[30] Foreign Application Priority Data

Aug. 13, 1979 [JP] Japan .................................. 54-103062

[51] Int. Cl.³ ............................................ C07C 51/255
[52] U.S. Cl. .................................................... 562/416
[58] Field of Search ......................................... 562/416

[56] References Cited

U.S. PATENT DOCUMENTS 2,962,361 11/1960 Spiller et al. ........................ 562/416
3,157,691 11/1964 Keith ................................... 562/416
3,584,038 6/1971 Barone et al. ....................... 562/416
3,678,106 7/1972 Ager .................................... 562/416

FOREIGN PATENT DOCUMENTS 740129 4/1970 Belgium ............................. 562/416
1468710 10/1970 Fed. Rep. of Germany ...... 562/416
47-19786 6/1972 Japan ................................. 562/416

*Primary Examiner*—Alan Siegel
*Attorney, Agent, or Firm*—Armstrong, Nikaido, Marmelstein & Kubovcik

[57] ABSTRACT

Aromatic polycarboxylic acids are produced in high yield by oxidation of polyalkyl-substituted aromatic aldehydes or polyalkyl-substituted aromatic carboxylic acids with molecular oxygen in water as a solvent in the presence of metal ions of manganese or cerium and a bromine ion-liberating compound as a catalyst, while keeping an oxygen concentration of effluent gas from reactor at least at 3%.

12 Claims, No Drawings

PROCESS FOR PRODUCING AROMATIC POLYCARBOXYLIC ACID

The present invention relates to a process for producing an aromatic polycarboxylic acid from a corresponding polyalkyl-substituted aromatic aldehyde.

Among aromatic polycarboxylic acids, trimellitic acid is widely used as a high grade plasticizer or a raw material for polyester, and pyromellitic acid is used as a special plasticizer or as a raw material for polyamide and polyimide.

The heretofore known processes for producing an aromatic polycarboxylic acid include a process for producing trimellitic acid by oxidizing pseudocumene with nitric acid or with air in an acetic acid solvent in the presence of a catalyst of cobalt-manganese-bromine system, and a process for producing pyromellitic acid by oxidizing durene, trimethylisopropylbenzene, etc. with air in gas phase or with nitric acid, among which the process by oxidation with nitric acid has, for example, an advantage of higher yield than the process by oxidation with air, but the oxidizing agent is nitric acid, and thus is obviously a problem in producing the aromatic polycarboxylic acid at a low cost.

On the other hand, the process by oxidation of pseudocumene with air is an application of the art of producing an aromatic dicarboxylic acid, for example, terephthalic acid to the oxidation of pseudocumene. Terephthalic acid can be substantially stoichiometrically obtained in one continuous stirred tank reactor relatively easily, that is, by means of a catalyst and a promoter at relatively low concentrations, whereas the oxidation of pseudocumene does not easily proceed, and many attempts have been so far made to improve the oxidation of pseudocumene. For example, Japanese Patent Publication No. 23732/70 proposes a complicated oxidation process in which the oxidation reaction is carried out at two stages, and catalyst components are changed at the individual stages. Japanese Laid-open Patent Application Specification No. 7173/71 proposes a two-stage or three-stage process. However, it has been found that it is difficult to oxidize pseudocumene and obtain trimerittic acid in a high yield such as at least 50% through reaction in one continuous stirred tank reactor according to the aforementioned prior art. The process by liquid phase oxidation of durene with air is far more difficult to carry out than the process by oxidation of pseudocumene, and is regarded as not practical. Thus, the process by gas phase oxidation of durene is generally carried out. However, it is difficult to obtain pure durene as a raw material and consequently the cost of durene is considerably high. Furthermore, more than 50% by mole of the fed raw material is completely combusted in the case of gas phase oxidation, and at most only 50% by mole of the raw material durene is converted to the desired product pyromellitic acid.

The present inventors have made various studies of producing aromatic polycarboxylic acids having at least three carboxyl groups such as pyromellitic acid, trimellitic acid, etc. at a low cost, and have found that yields of the aromatic polycarboxylic acids having at least three carboxyl groups can be drastically increased by oxidizing polyalkyl-substituted aromatic aldehydes or polyalkyl-substituted aromatic carboxylic acid as a raw material with air in a liquid phase under specific reaction conditions, and have established the present invention.

The present invention provides a process for producing an aromatic polycarboxylic acid having at least three carboxyl groups, which comprises oxidizing a polyalkyl-substituted aromatic aldehyde or polyalkyl-substituted aromatic carboxylic acid with molecular oxygen in water as a solvent in the presence of metal ions of manganese or cerium, and a bromine ion-liberating compound while maintaining an oxygen concentration of an effluent gas from a reactor at least at 3%.

The polyalkyl-substituted aromatic aldehyde to be used as the raw material in the oxidation reaction according to the present invention includes 2,4-dimethylbenzaldehyde, 3,4-dimethylbenzaldehyde, 2,4,5-trimethylbenzaldehyde, 2,4,6-trimethylbenzaldehyde, etc. The polyalkyl-substituted carboxylic acid includes 2,4-dimethylbenzoic acid, 3,4-dimethylbenzoic acid, 2,4,5-trimethylbenzoic acid, 2,4,6-trimethylbenzoic acid, etc.

The polyalkyl-substituted aromatic aldehyde can be substantially stoichiometrically synthesized without any production of isomers as by-product by reacting a polyalkyl-substituted aromatic hydrocarbon with carbon monoxide in the presence of a catalyst of $HF-BF_3$ system. For example, 2,4-dimethylbenzaldehyde and 3,4-dimethylbenzaldehyde obtained by addition reaction of metaxylene and orthoxylene with carbon monoxide in the presence of a catalyst of $HF-BF_3$ system is most preferable as the raw material for trimellitic acid, and 2,4,5-trimethylbenzaldehyde obtained by addition reaction of pseudocumene with carbon monoxide in the presence of a catalyst of $HF-BF_3$ system is most preferable as the raw material for pyromellitic acid. 2,4,6-Trimethylbenzaldehyde is obtained in high yield by hydroformylation of mesitylene in the same manner as above, and can be converted to mellophannic acid by oxidation according to the present invention.

As the catalyst for the present invention, metal ions of mangnese, such as manganese chloride, manganese bromide, manganese iodide, manganese acetate, manganese sulphate, manganese nitrate, or cerium, such as cerium chloride, cerium bromide, cerium iodide, cerium acetate, cerium sulphate, cerium nitrate, are used, as described above. If manganese bromide or cerium bromide are used as the catalyst, the further addition of bromine ion-liberating compound is not necessary. Some metals such as palladium, ruthenium, bismuth, niobium, thallium, tellurium, vanadium, etc. are strongly combined with bromine ions, and cannot be used as the catalyst. As the bromine ion-liberating compound, any compound can be used, so far as it can liberate bromine ions in the course of oxidation reaction. For example, hydrogen bromide, ammonium bromide, sodium bromide, or organobromo compounds such as alkyl bromide, etc. can be used.

Function and effect of the catalyst in the present invention is greatly different from those in the case of aromatic dicarboxylic acid. For example, when terephthalic acid is synthesized from p-tolualdehyde, the reaction proceeds in the presence of only a bromine ion-liberating compound and terephthalic acid can be obtained in high yield without intensive addition of the metal ions. On the contrary, when an aromatic polycarboxylic acid is synthesized from the corresponding polyalkyl-substituted aromatic aldehyde or polyalkyl-substituted aromatic carboxylic acid, it is necessary to conduct the reaction in the co-presence of metal ions and bromine ion-liberating compound as the catalyst.

In the present invention, 0.5–12% by weight, preferably 0.5–6% by weight, of the bromine ion-liberating compound in terms of bromine ions, must be present as the catalyst on the basis of water as the solvent. The metal ions of manganese or cerium must be present at the same time in g-equivalent or less than g-equivalent to the bromine ion-liberating compound in terms of bromine ions.

Water is used as the solvent in the present invention, because there is no loss of the solvent by combustion due to the oxidation. The amount of water as the solvent is not particularly restricted, but it is preferable to use water in weight equal to or more than that of the raw material polyalkyl substituted aromatic aldehyde or polyalkyl-substituted aromatic carboxylic acid.

In the present invention, it is essential to use said metal ions of manganese or cerium and a bromine ion-liberating compound as the catalyst, and also to conduct the reaction while maintaining an oxygen concentration of the effluent gas from a reactor at least at 3%. These requirements are not essential for the production of aromatic dicarboxylic acid, that is, there is no problem at all even if the reaction is conducted at an oxygen concentration of the effluent gas of less than 3%, whereas in the production of an aromatic polycarboxylic acid according to the present invention, tarry matter is formed when the oxygen concentration of the effluent gas is less than 3%, and the yield of the aromatic polycarboxylic acid is lowered. A higher oxygen concentration of the effluent gas has no special problem, but the oxygen concentration of the effluent gas of more than 10%, if it occurs while the raw material aromatic aldehyde or aromatic carboxylic acid is introduced into the reactor, means that the effluent gas is within the explosion limit. Thus, it is preferable to keep the oxygen concentration of the effluent gas not more than 8% while the oxydation reaction is being carried out.

In the present invention, reaction temperature is 180°–280° C., preferably 210°–260° C. Reaction pressure is automatically set by keeping the reaction temperature constant generally by evaporation and condensation and refluxing operation of water as the solvent, but it is also possible to keep the reaction pressure at a desired value by the external heat exchanger. Any pressure can be applied so far as it is within a pressure range in which the reaction solution can be kept in a liquid phase, and usually a pressure of 10–70 kg/cm$^2$ gage is used.

As the oxidizing agent, either oxygen or air can be used, but use of air is more economical.

The reaction can be carried out batchwise, semi-continuously, or continuously, but the best effect can be obtained particularly when the present invention is applied to the continuous oxidation process.

The present invention will be described in detail below, referring to Examples.

EXAMPLE 1

Into an autoclave made from zirconium having a net capacity of 2 l with a reflux condenser, a stirrer, a heater, a raw material inlet, a gas inlet, a gas outlet and a product outlet were charged 671 g of water and 38 g of manganese bromide tetrahydrate. Nitrogen was introduced under pressure into the autoclave at the gas inlet to elevate the inside pressure of the autoclave to 10 kg/cm$^2$ gage. The autoclave was heated to 230° C. and then, air was introduced into the autoclave at the gas inlet to replace the nitrogen with the air in the autoclave, and 2,4,5-trimethylbenzaldehyde (purity: 99.5%) was charged into the autoclave at a rate of 260 g/hr for one hour while continuing the introduction of the air therein, and keeping the reaction pressure at 43 kg/cm$^2$ gage and the oxygen concentration of effluent gas at 4–5%. The introduction of air was continued for further about 10 minutes after the end of charging 2,4,5-trimethylbenzaldehyde, and stopped after the oxygen concentration of the effluent gas was returned to 21%. The autoclave was then cooled, and the reaction product was taken out of the autoclave. The reaction product was in a slurry state, and was subjected to solid-liquid separation. The resulting solid matter was washed with cold water and dried at 65° C. 400 g of the solid matter was obtained and found to be pyromellitic acid dihydrate. In addition, the reaction mother liquor and the resulting washing water contained 20 g of pyromellitic acid dihydrate, and molar yield of pyromellitic acid from 2,4,5-trimethylbenzaldehyde was 82.5%.

EXAMPLE 2

Oxidation of 2,4,5-trimethylbenzaldehyde was semi-continuously carried out in the same autoclave in the same manner as used in Example 1, except that 671 g of water, 19 g of manganese bromide tetrahydrate and 10 g of hydrogen bromide were charged into the autoclave at a reaction temperature of 240° C. under a reaction pressure of 53 kg/cm$^2$ gage.

The resulting pyromellitic acid dihydrate was in an amount of 390 g as solid and 20 g as dissolved in the liquors, total being 410 g, and thus the molar yield of pyromellitic acid from 2,4,5-trimethylbenzaldehyde was 80.5%.

Comparative Example 1

The reaction was conducted in the same apparatus in the same manner as used in Example 1 at a reaction temperature of 230° C. by charging 671 g of water and 20 g of hydrogen bromide without charging any manganese salt. Oxygen absorption rate was slow in contrast to that when the manganese salt was added. Introduction of air was continued for further 10 minutes after the end of charging 2,4,5-trimethylbenzaldehyde, and the autoclave was cooled. Then, the reaction product was taken out of the autoclave, and was found in a tarry state, and no solid pyromellitic acid was obtained.

EXAMPLE 3

In the same autoclave as used in Example 1 were charged 500 g of water, 7 g of hydrogen bromide and 15 g of manganese bromide tetrahydrate. The autoclave was pressurized with nitrogen and heated. After the autoclave was heated to a temperature of 230° C., 2,4-dimethylbenzaldehyde (purity: more than 99.5%) was charged into the autoclave at a rate of 250 g/hr, and also a catalyst solution with the same composition as charged initially into the autoclave (500 g of water, 7 g of HBr and 15 g of MnBr$_2$.4H$_2$O) was separately charged thereto at a rate of 500 g/hr. Air was introduced into the autoclave at the same time when 2,4-dimethylbenzaldehyde was charged into the autoclave, and the flow rate of the air was controlled so that the oxygen concentration of the effluent gas from the autoclave may be kept at 3–4%. A reaction product was withdrawn from the autoclave at a rate of about 890 g/hr while maintaining the liquid level constant in the autoclave.

The reaction product was in a slurry state when cooled, and was subjected to solid-liquid separation by filtration, whereby trimellitic acid was obtained at a rate of 370 g/hr. This means that 94.4% of 2,4-dimethylbenzaldehyde charged as the raw material was converted to trimellitic acid.

EXAMPLE 4

Oxidation of 2,4,5-trimethylbenzaldehyde was carried out in the same autoclave in the same manner as used in Example 1, except that 670 g of water, 10 g of hydrogen bromide and 58 g of manganese bromide tetrahydrate were charged into the autoclave. Pyromellitic acid was obtained in a yield of 81% by mole on the basis of the raw material 2,4,5-trimethylbenzaldehyde.

EXAMPLE 5

Oxidation of 2,4,5-trimethylbenzaldehyde was carried out in the same autoclave in the same manner as used in Example 1, except that 670 g of water, 5 g of hydrogen bromide, and 31 g of cerous bromide pentahydrate were charged into the autoclave. Yield of pyromellitic acid was 82% by mole on the basis of the raw material 2,4,5-trimethylbenzaldehyde.

EXAMPLE 6

Oxidation reaction of 2,4,5-trimethylbenzaldehyde was continuously carried out with the same catalyst composition in the same manner as used in Example 3. That is, 500 g/hr of the same catalyst solution as in Example 3 and 250 g/hr of 2,4,5-trimethylbenzaldehyde were separately charged into the same autoclave as used in Example 3, and about 960 g/hr of the reaction product was taken out of the autoclave. Pyromellitic acid dihydrate was formed at a rate of 402 g/hr on average. This means that 82.1% by mole of 2,4,5-trimethylbenzaldehyde was converted to pyromellitic acid.

EXAMPLE 7

Into the same autoclave as used in Example 1 were charged 670 g of water, 2 g of hydrogen bromide and 33 g of manganese bromide tetrahydrate. 250 g/hr of 2,4-dimethylbenzaldehyde was charged into the autoclave at a reaction temperature of 230° C. for one hour, and subjected to oxidation with air, while keeping the oxygen concentration of the effluent gas from the autoclave at 3-4%.

Total 372 g of trimellitic acid, that is, total of that as the solid and that contained in the mother liquor, was formed, and the molar yield of trimellitic acid from the raw material 2,4-dimethylbenzaldehyde was 95%.

Comparative Example 2

Oxidation of 2,4,5-trimethylbenzaldehyde was semi-continuously carried out in the same manner as in Example 2 with the same catalyst as used in Example 2 at a reaction temperature of 240° C. under a reaction pressure of 53 kg/cm² gage, except that the oxygen concentration of the effluent gas from the autoclave was kept at 1-2%. Introduction of air was continued for further 10 minutes after the end of charging 2,4,5-trimethylbenzaldehyde, and then the autoclave was cooled. Reaction product was then taken out of the autoclave, and it was found that the tarry matter with an irritating smell was formed, and no solid pyromellitic acid was formed.

Comparative Example 3

Oxidation of p-tolualdehyde (purity: 99.2%) was semi-continuously carried out in the same manner as in Example 2 with the same catalyst as used in Example 2 at a reaction temperature of 240° C. under a reaction pressure of 53 kg/cm² gage, except that p-tolualdehyde was charged into the autoclave at a rate of 266 g/hr for one hour and the oxygen concentration of the effluent gas from the autoclave was kept at 1-2%. Introduction of air was continued for further 10 minutes after the end of charging p-tolualdehyde, and then stopped. After cooling the autoclave, a reaction product was taken out of the autoclave.

As the product, 350 g of terephthalic acid was obtained, which corresponded to molar yield of 95%. In the oxidation of p-tolualdehyde, terephthalic acid could be synthesized in good yield even by keeping the oxygen concentration of the effluent gas from the autoclave at less than 3%.

What is claimed is:

1. A process for producing an aromatic polycarboxylic acid having at least three carboxyl groups, which comprises oxidizing a polyalkyl-substituted aromatic aldehyde or a polyalkyl-substituted aromatic carboxylic acid with molecular oxygen in water as a solvent in the presence of metal ions of manganese or cerium and a bromide ion-liberating compound as a catalyst, while keeping an oxygen concentration of effluent gas from reactor at least at 3%.

2. The process according to claim 1, wherein the polyalkyl-substituted aromatic aldehyde is 2,4-dimethylbenzaldehyde, 3,4-dimethylbenzaldehyde, 2,4,5-trimethylbenzaldehyde or 2,4,6-trimethylbenzaldehyde.

3. The process according to claim 1, wherein the polyalkyl-substituted aromatic acid is 2,4-dimethylbenzoic acid, 3,4-dimethylbenzoic acid, 3,4,5-trimethylbenzoic acid, or 2,4,6-trimethylbenzoic acid.

4. The process according to claim 1, wherein the bromine ion-liberating compound is hydrogen bromide, ammonium bromide, sodium bromide, or alkyl bromide.

5. The process according to claim 4, wherein the bromine ion-liberating compound is used in an amount of 0.5-12% by weight in terms of bromine ions on the basis of the water as the solvent.

6. The process according to claim 5, wherein the bromine ion-liberating compound is used in an amount of 0.5-6% by weight in terms of bromine ions on the basis of the water as the solvent.

7. The process according to claim 1, wherein the metal ions of manganese or cerium is used in g-equivalent or less than that to the bromine ion-liberating compound in terms of bromine ions.

8. The process according to claim 1, wherein the water is used in weight equal to or more than that of the polyalkyl-substituted aromatic aldehyde or the polyalkyl-substituted aromatic acid.

9. The process according to claim 1, wherein the oxidation is carried out at a reaction temperature of 180°-280° C. under a pressure of 10-70 kg/cm² gage.

10. The process according to claim 1, wherein the molecular oxygen is in the form of air.

11. The process according to claim 1, wherein the oxygen concentration of effluent gas from reactor is kept at 3-8%, while the oxydation reaction is being carried out.

12. A process for producing an aromatic polycarboxylic acid having at least three carboxyl groups, which comprises oxidizing a polyalkyl-substituted aromatic aldehyde or a polyalkyl-substituted aromatic carboxylic acid at 180°-280° C. with molecular oxygen in water as a solvent in the presence of metal ions of manganese or cerium and a bromine ion-liberating compound as a catalyst, the bromine ion-liberating compound being present in an amount to provide 0.5–12% by weight of bromine ions on the basis of the water and the manganese or cerium ions being present in a gram equivalent ratio of 1:1 or less than that to the bromine ion-liberating compound in terms of bromine ions, while keeping an oxygen concentration of effluent gas from reactor at 3–8%.

* * * * *